United States Patent
Steenstra Toussaint (10) Patent No.: US 10,646,394 B2
(45) Date of Patent: May 12, 2020

(54) APPARATUS, SYSTEM AND METHOD OF PROVIDING A FOOT PEDAL PLATFORM FOR OPHTHALMIC SURGERY

(71) Applicant: ABBOTT MEDICAL OPTICS INC., Santa Ana, CA (US)

(72) Inventor: Tyson J. Steenstra Toussaint, Westminster, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 162 days.

(21) Appl. No.: 15/494,378

(22) Filed: Apr. 21, 2017

(65) Prior Publication Data
US 2018/0303694 A1   Oct. 25, 2018

(51) Int. Cl.
   *A61G 15/12*   (2006.01)
   *H01H 3/14*   (2006.01)
   (Continued)

(52) U.S. Cl.
   CPC .............. *A61G 15/10* (2013.01); *A47C 7/004* (2013.01); *A47C 7/006* (2013.01); *A47C 7/50* (2013.01); *A47C 7/62* (2013.01); *A61B 17/00* (2013.01); *A61B 90/50* (2016.02); *A61B 90/60* (2016.02); *A61F 9/00745* (2013.01); *A61B 2017/00199* (2013.01); *A61B 2017/00221* (2013.01); *A61B 2017/00858* (2013.01); *A61B 2017/00973* (2013.01); *A61B 2017/00977* (2013.01); *H01H 3/14* (2013.01)

(58) Field of Classification Search
   CPC ....... A47C 7/50; A47C 7/5066; A47C 7/5064; A47C 7/5062; A47C 7/006; A61G 15/12; H01H 3/14; A61B 2017/00973
   See application file for complete search history.

(56) References Cited

U.S. PATENT DOCUMENTS

| 2,087,932 A | 7/1937 | Albert et al. |
| 2,498,550 A | 2/1950 | Johnson et al. |

(Continued)

FOREIGN PATENT DOCUMENTS

| DE | 1110818 B | 7/1961 |
| DE | 202009009341 U1 | 11/2010 |

(Continued)

OTHER PUBLICATIONS

CTADigital: "Heavy-Duty Arm Mount with Lock for Tablets", Mar. 22, 2016 (Mar. 22, 2016), XP054978457, [retrieved on Jun. 27, 2018]. Retrieved from the Internet: [URL:https://www.youtube.com/watch?v=IVv0V9c6-qk].

(Continued)

*Primary Examiner* — Timothy J Brindley
(74) *Attorney, Agent, or Firm* — Johnson & Johnson Surgical Vision, Inc.

(57) ABSTRACT

The disclosed apparatus, system and method may include at least an adjustable platform for a surgical footpedal, such as may be associated with a phacoemulsification surgical console. The adjustable platform for a surgical footpedal may include a bearing arm having a mount; a pedal, having associated therewith one or more sensors indicative of at least one surgical setting; and a platform at a first end of the bearing arm distal from the mount, comprising a mating surface for receiving the pedal.

22 Claims, 6 Drawing Sheets

(51) Int. Cl.
- *A47C 7/50* (2006.01)
- *A61G 15/10* (2006.01)
- *A61F 9/007* (2006.01)
- *A47C 7/00* (2006.01)
- *A47C 7/62* (2006.01)
- *A61B 90/60* (2016.01)
- *A61B 17/00* (2006.01)
- *A61B 90/50* (2016.01)

(56) References Cited

U.S. PATENT DOCUMENTS

| | | | |
|---|---|---|---|
| 2,620,863 A | 12/1952 | Cooper et al. | |
| 3,712,669 A * | 1/1973 | Cates | A47C 1/04 297/188.21 |
| 3,820,844 A | 6/1974 | Fortnam et al. | |
| 4,854,301 A * | 8/1989 | Nakajima | A61B 1/00147 600/102 |
| 5,271,379 A * | 12/1993 | Phan | A61B 1/12 600/104 |
| 6,784,388 B1 * | 8/2004 | Braaten | H01H 3/14 200/335 |
| 7,084,364 B2 * | 8/2006 | Mezhinsky | H01H 3/14 200/310 |
| 7,708,404 B2 * | 5/2010 | Gaida | A61F 9/008 351/205 |
| 8,465,473 B2 * | 6/2013 | Horvath | A61B 17/32002 200/86.5 |
| 8,680,412 B2 * | 3/2014 | Horvath | A61B 17/00 200/86.5 |
| 8,749,188 B2 | 6/2014 | Tran et al. | |
| 9,271,806 B2 | 3/2016 | Tran et al. | |
| 9,393,152 B2 | 7/2016 | Wong et al. | |
| 9,642,465 B1 * | 5/2017 | Park | A47C 7/506 |
| 2003/0111327 A1 * | 6/2003 | Metzler | H01H 3/14 200/86.5 |
| 2005/0189808 A1 * | 9/2005 | Lin | A47C 7/506 297/423.21 |
| 2005/0253441 A1 | 11/2005 | Benden et al. | |
| 2011/0163577 A1 | 7/2011 | Anastasov et al. | |
| 2016/0089294 A1 | 3/2016 | Guillaume | |
| 2017/0105530 A1 * | 4/2017 | Sheinkop | A47C 1/022 |
| 2018/0312372 A1 * | 11/2018 | Wilson | B66B 9/0853 |

FOREIGN PATENT DOCUMENTS

| | | | |
|---|---|---|---|
| JP | 58013230 A | 1/1983 | |
| JP | H0557728 A | 3/1993 | |
| WO | 2011116332 A2 | 9/2011 | |
| WO | WO-2013058890 A1 * | 4/2013 | H01H 3/14 |
| WO | 2014172550 A1 | 10/2014 | |
| WO | 2014175846 A1 | 10/2014 | |

OTHER PUBLICATIONS

Haag: "COMBISIT", Nov. 20, 2012 (Nov. 20, 2012), XP055488799, [retrieved on Jun. 28, 2018]. Retrieved from the Internet: [URL:https://www.haag-streit.com/fileadmin/Haag-Streit_USA/Microscopes/stools/download/Brochure_Combisit.pdf].

Partial International Search Report for Application No. PCT/US2018/028256, dated Jul. 9, 2018, 20 pages.

[ Pdf., et al.: Google Search result "Brochure_Combisit.pdf" vol. 4, Sep. 2018, XP055488795, [retrieved on Jun. 28, 2018] Retrieved from the Internet: URL: [https://www.google.com/search?tbs=cdr°/03A1°/02Ccd_mee/03A21.04.2107&d=IKg0W65WkcfBAcivejegH&q.Broch....

Anonymous: "Information & Updates—Wolf Hardware", Mar. 22, 2017 (Mar. 22, 2017), XP055510648, Retrieved from the Internet: URL:https://www.wolfhardware.net/new-blog/[retrieved on Sep. 27, 2019].

International Search Report and written opinion for Application No. PCT/US2018/028256, dated Oct. 10, 2018, 32 pages.

VRvibe: "Top VR Motion Chairs Virtual Reality",Youtube, Oct. 22, 2016 (Oct. 22, 2016), p. 1, XP054978727, Retrieved from the Internet:URL:https://www.youtube.com/watch?v=CXoLj8mQDus [retrieved on Sep. 27, 2018].

* cited by examiner

APPARATUS, SYSTEM AND METHOD OF PROVIDING A FOOT PEDAL PLATFORM FOR OPHTHALMIC SURGERY

BACKGROUND

Field of the Disclosure

The present disclosure relates to medical devices and systems, and, more specifically, to an apparatus, system and method of providing a foot pedal platform for ophthalmic surgery.

Description of the Background

Phacoemulsification is a medically recognized technique utilized for crystalline lens removal, and is one type of ophthalmic surgery. Phacoemulsification includes making a corneal and/or scleral incision, and the insertion of a phacoemulsification handpiece, which is typically comprised of a needle that is ultrasonically driven, in order to emulsify, i.e., to liquefy, the natural crystalline lens and/or an unhealthy aspect, such as a cataract, associated therewith.

The phacoemulsification handpiece is generally coupled to an irrigation source and an aspiration pump. The handpiece includes a distal tip for insertion within the anterior chamber of the patient's eye that emits ultrasonic energy to emulsify the crystalline lens. The handpiece further includes a sleeve that surrounds at least a portion of the needle and comprises at least one irrigation port near the distal end, which is coupled to an irrigation source via an irrigation line, and an aspiration port at the distal tip of the needle, which is coupled to an aspiration pump via an aspiration line. Fluid from the irrigation source, which is typically an elevated bottle of saline solution, is irrigated into the eye via the irrigation line and the irrigation port, and the irrigation fluid and emulsified crystalline lens material are aspirated from the eye by the aspiration pump via the aspiration port and the aspiration line.

Other ophthalmic surgical techniques also typically include irrigation and aspiration of the eye. Such other ophthalmic procedures may or may not include the destruction, alteration or removal of features of the natural eye.

Ophthalmic surgical systems typically provide a control console to control the aforementioned one or more fluid pressure-operated surgical instruments. The control console provides the pressure signals for operating the instruments, and may include several different types of human actuatable controllers for controlling these signals. One such actuatable controller is often a footpedal assembly, which the surgeon can use to control the referenced surgical instrumentation.

Conventional footpedal assemblies may use a variety of pneumatic and/or electrical actuators to provide the control signals. In pneumatic footpedal assemblies, pneumatic fluid enters the footpedal assembly through an inlet port, which is connected to a pneumatic supply. The amount of pneumatic fluid leaving the footpedal assembly is proportional to the amount of depression on the footpedal of the assembly. That is, the larger the depression of the footpedal, the greater the amount of pneumatic fluid that is delivered to the control console from the footpedal assembly.

Footpedal assemblies which employ electrical actuators may use a potentiometer attached to the pedal. In this case, as the pedal is pressed by the operator, the resistance of the potentiometer changes. This change in resistance is used by the control console to generate a signal for adjusting the surgical instruments.

More particularly, ophthalmic surgery may employ footpedals for the actuation of specific surgical modes, and/or for specific delineations within surgical modes. Multimode functions required in phacoemulsification, by way of non-limiting example, may include irrigation and aspiration and specific delineations thereof, as discussed herein above. Thus, a footpedal may be employed throughout an ophthalmic surgical procedure, and as such the footpedal may require adjustment throughout the surgical process.

Therefore, during a surgical procedure such as phacoemulsification, the footpedal may need to be frequently physically readjusted as a doctor moves about during the surgery, such as to allow for continuous use by the doctor throughout the surgery. For example, when a doctor needs to move a chair, or move while standing, around the operating table, the physical position of the surgical footpedal may need to be readjusted according the new location of the doctor and/or her chair.

In typical embodiments, once a doctor or staff enters the active operating room immediately prior to or during a surgical procedure, the doctor and staff must remain sterile and hence can't touch the foot pedal, other than with the feet, if the foot pedal needs to be moved to a different location or otherwise adjusted. Moreover, the manual readjustment of a footpedal, such as before or during surgery, is often difficult because only the feet of the adjusting person may be used to adjust position if that person is to remain sterile for the procedure.

Yet further, it is typical that the alignment and positioning of the footpedal will initially be done by a staff person, who may differ in height or shoe size from the doctor. But after this initial approximate position is set, the doctor may finalize the positioning of a footpedal, and/or may readjust a footpedal as necessary, only with her foot and typically while sitting, as previously mentioned. If the footpedal must be grossly adjusted, such as during surgery, a doctor will often need staff assistance with the gross movements, due to the limited adjustability of the footpedal.

Therefore, the need exists for an apparatus, system, and method of enabling adjustment and readjustment of a footpedal during surgical procedures.

SUMMARY

The disclosed apparatus, system and method may include at least an adjustable platform capable of receiving a surgical footpedal. The adjustable platform may include a bearing arm having at a first end thereof an adjustable mount suitable for mounting to a surgical chair; and a platform at a second end of the bearing arm distal from the first end, the platform being capable of receiving the surgical footpedal and comprising a mating portion for receiving the surgical footpedal.

The disclosed apparatus, system and method may additionally include at least an adjustable surgical footpedal, such as may be associated with a phacoemulsification surgical console. The adjustable surgical footpedal may include a bearing arm having a mount; a pedal, having associated therewith one or more sensors indicative of at least one surgical setting; and a platform at a first end of the bearing arm distal from the mount, comprising a mating surface for receiving the pedal.

More particularly, an exemplary surgical chair according to certain of the embodiments may include a seat; a backrest perpendicularly associated with the seat; a plurality of wheels; a rigid brace connectively associating the plurality of wheels with the seat; a bearing arm having a mount suitable for mounting the bearing arm to the chair; a pedal having associated therewith one or more sensors indicative of at least one surgical setting; and a platform at a first end of the bearing arm distal from the mount, comprising a mating surface for receiving the pedal.

Thus, the disclosed embodiments provide an apparatus, system, and method of enabling adjustment and readjustment of a foot pedal during surgical procedures.

BRIEF DESCRIPTION OF THE FIGURES

Referring now to the figures incorporated herein, shown are non-limiting embodiments of the present disclosure, wherein like numerals represent like elements, and wherein.

DETAILED DESCRIPTION

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens with a handpiece. Once the lens is emulsified, it is aspirated from the eye by applying a vacuum to a handpiece to aspirate the emulsified lens material. During the procedure, irrigation is performed, using a solution, such as a balanced salt solution, during aspiration thereby maintaining pressure in the interior of the eye. The emulsified and aspirated lens is then typically replaced with a clear artificial intraocular lens (IOL).

To perform the afore-discussed and similar procedures, a surgeon often utilizes a computer-controlled system of specialized equipment called a phacoemulsification system to control and execute the ultrasonic emulsification and aspiration of the natural lens of the eye prior to inserting the IOL. Phacoemulsification systems use various computer programs for performing these various tasks, which are controlled in part by adjusting settings of these programs to drive motors and pumps, for example, which emulsify and aspirate the subject lens material and which do other tasks necessary to complete the surgery. These control programs may receive control signals from the system console, and/or from peripheral elements linked to the system console. Such peripheral control elements may include, by way of example, one or more footpedals.

During the procedure, information such as the amount of vacuum applied to aspirate, the flow rate, a microscopic view of the operating field, and the like, may be displayed on and at least partially controllable from a user interface of the phacoemulsification system console, or on a separate screen, computer, or other viewing device. At least some of this data is commonly used to inform and improve ongoing and subsequent procedures.

Figure 1:
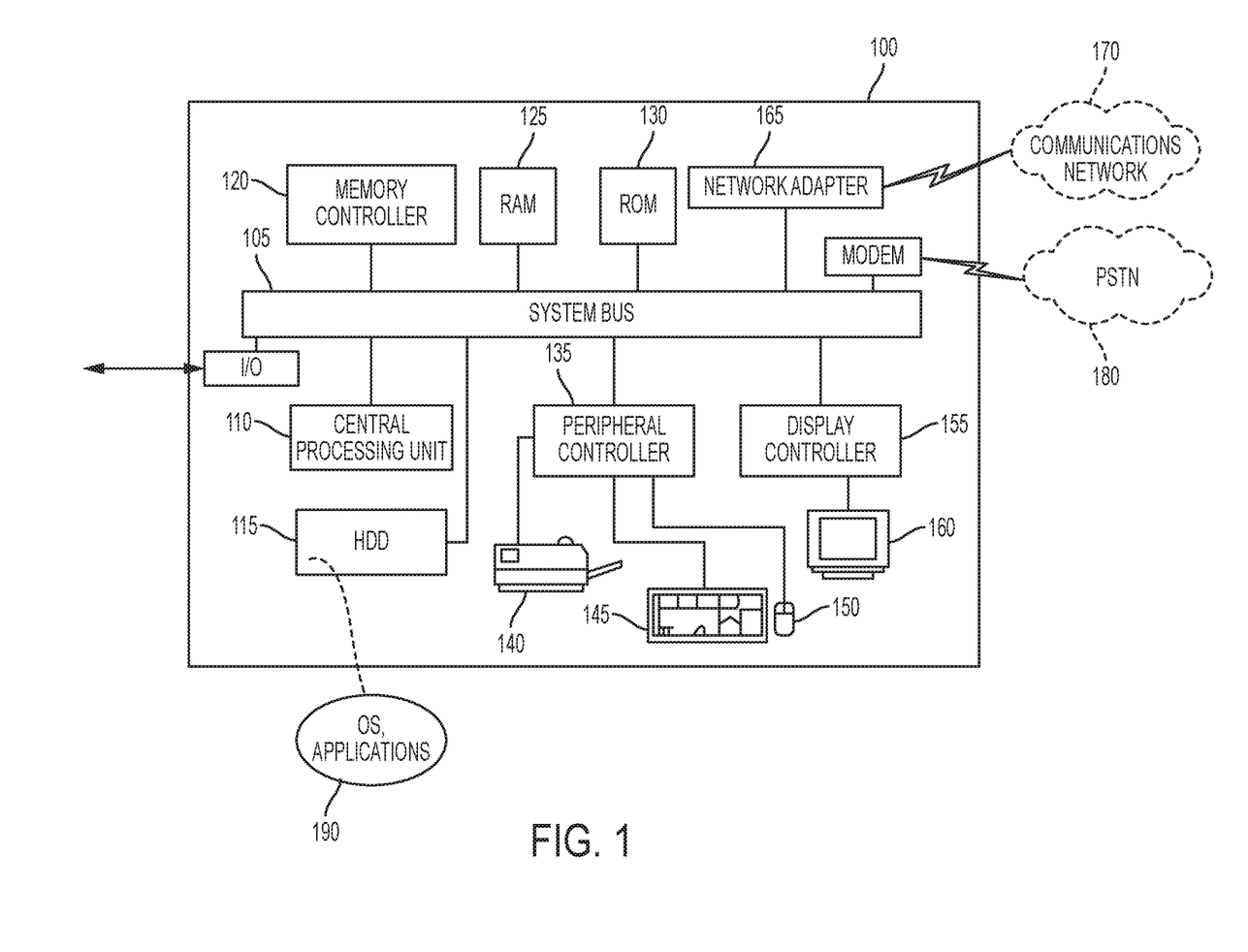
FIG. 1 depicts an exemplary computing system for use in association with an ophthalmic surgical console.

FIG. 1 depicts an exemplary computing system 100 for use in association with an ophthalmic surgical console in accordance with herein described system and methods. Computing system 100 is capable of executing software, such as an operating system (OS) and one or more computing applications 190. The operation of exemplary computing system 100 is controlled primarily by computer readable instructions, such as instructions stored in a computer readable storage medium, such as hard disk drive (HDD) 115, optical disk (not shown) such as a CD or DVD, solid state drive (not shown) such as a USB "thumb drive," or the like. Such instructions may be executed within central processing unit (CPU) 110 to cause computing system 100 to perform operations. In many known computer servers, workstations, personal computers, and the like, CPU 110 is implemented in an integrated circuit called a processor.

It is appreciated that, although exemplary computing system 100 is shown to comprise a single CPU 110, such description is merely illustrative, as computing system 100 may comprise a plurality of CPUs 110. Additionally, computing system 100 may exploit the resources of remote CPUs (not shown), for example, through communications network 170 or some other data communications means.

In operation, CPU 110 fetches, decodes, and executes instructions from a computer readable storage medium such as HDD 115. Such instructions may be included in software such as an operating system (OS), executable programs, and the like. Information, such as computer instructions and other computer readable data, is transferred between components of computing system 100 via the system's main data-transfer path. The main data-transfer path may use a system bus architecture 105, although other computer architectures (not shown) can be used, such as architectures using serializers and deserializers and crossbar switches to communicate data between devices over serial communication paths. System bus 105 may include data lines for sending data, address lines for sending addresses, and control lines for sending interrupts and for operating the system bus. Some busses provide bus arbitration that regulates access to the bus by extension cards, controllers, and CPU 110. Devices that attach to the busses and arbitrate access to the bus are called bus masters. Bus master support also allows multiprocessor configurations of the busses to be created by the addition of bus master adapters containing processors and support chips.

Memory devices coupled to system bus 105 may include random access memory (RAM) 125 and/or read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode may normally access only memory mapped by its own process virtual address space; in such instances, the program cannot access memory within another process' virtual address space unless memory sharing between the processes has been set up.

In addition, computing system 100 may contain peripheral communications bus 135, which is responsible for communicating instructions from CPU 110 to, and/or receiving data from, peripherals, such as peripherals 140, 145, and 150, which may include printers, keyboards, and/or the peripheral surgical elements, such as one or more footpedals, discussed herein throughout. An example of a peripheral bus is the Peripheral Component Interconnect (PCI) bus.

Display 160, which is controlled by display controller 155, may be used to display visual output and/or presentation generated by or at the request of computing system 100, responsive to operation of the aforementioned computing program. Such visual output may include text, graphics, animated graphics, and/or video, for example. Display 160 may be implemented with a CRT-based video display, an LCD or LED-based display, a gas plasma-based flat-panel display, a touch-panel display, or the like. Display controller 155 includes electronic components required to generate a video signal that is sent to display 160.

Further, computing system 100 may contain network adapter 165 which may be used to couple computing system 100 to external communication network 170, which may include or provide access to the Internet, an intranet, an extranet, or the like. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

Network adaptor 165 may communicate to and from network 170 using any available wired or wireless technologies. Such technologies may include, by way of non-limiting example, cellular, Wi-Fi, Bluetooth, infrared, or the like.

It is appreciated that exemplary computing system 100 is merely illustrative of a computing environment in which the herein described systems and methods may operate, and does not limit the implementation of the herein described systems and methods in computing environments having differing components and configurations. That is to say, the inventive concepts described herein may be implemented in various computing environments using various components and configurations.

Figure 2:
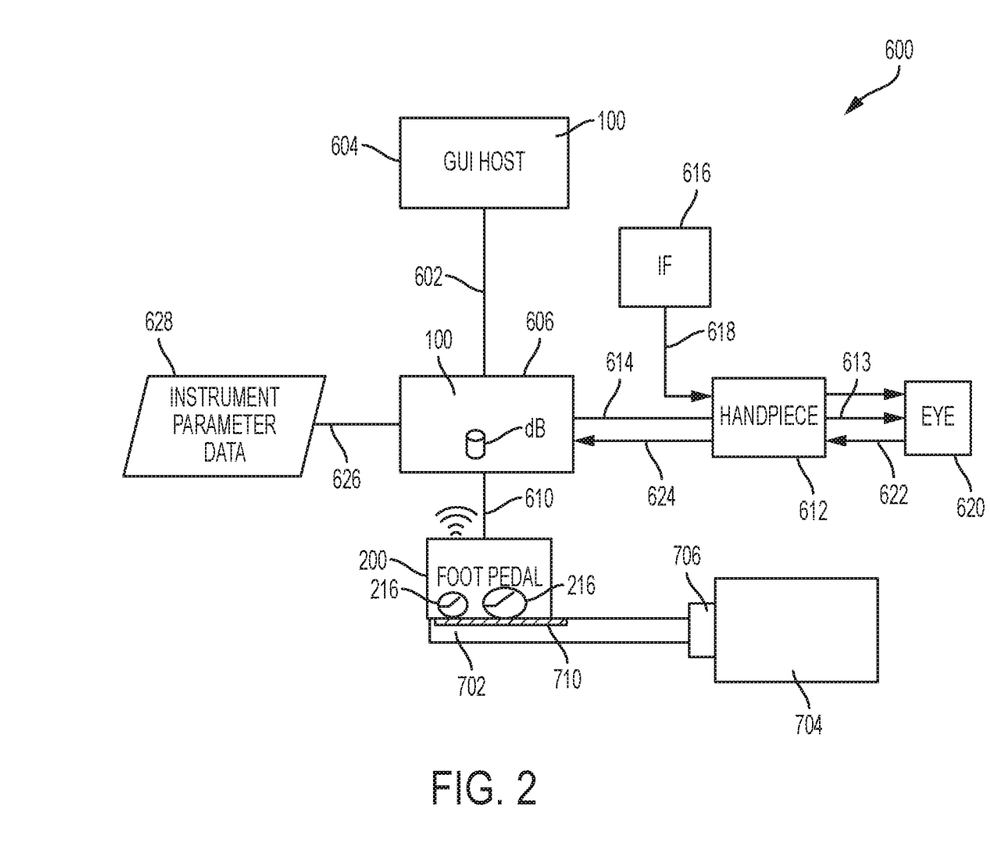
FIG. 2 illustrates the use of a peripheral in the form of a footpedal with an ophthalmic surgical console.

As illustrated in FIG. 2, one peripheral that may communicate using peripheral communications bus 130 is a footpedal. The actuation of the footpedal 200 by, for example, a user's foot, may have corresponded thereto by the actuation a travel distance, which may be visually indicated on at least one graphical user interface (GUI) 604 of the phacoemulsification system 600 communicatively associated with the footpedal 200. The system may employ the computer system 100 discussed above, by way of example.

Moreover, the programmable travel positions of the footpedal 200 may control different functions provided by the console 606, and/or may be additive in functionality. For example, a first travel position for footpedal 200 may be programmed to have the console 606 provide a specific irrigation function, a second position may add an aspiration function, and a third position may add another function to the aspiration and irrigation function, e.g. ultrasound. In addition, other switches 216 may allow for control of the functions activated via the footpedal 200. For example, if an aspiration function is activated, at least one other switch 216 may be programmed to control the strength of the vacuum applied or change modes.

Although the present footpedal control may be used in various surgical environments and applications, a particularly useful application is in an ocular surgical system, such as a phacoemulsification/vitrectomy system. In an exemplary phacoemulsification system 600, a serial communication cable 602 may connect a GUI 604 and console 606 for the purposes of controlling the console 606, at least in part, by the GUI host 604. The console 606 may be considered a computational device in the arrangement shown, but other arrangements are possible. A switch module associated with an exemplary footpedal 200, such as described herein, transmits control signals relating internal physical and virtual switch position information as input to the console 606 over a serial communications cable 610, or wirelessly if desired.

The system 600 has a handpiece 612 that typically includes a needle tip 613 and electrical means, such as a piezoelectric crystal, for ultrasonically vibrating the needle. The console 606 causes the supply of power on line 614 to the operative tip 613. An irrigation fluid source 616 can be fluidly coupled to handpiece 612 through line 618. The irrigation fluid 618 and ultrasonic power 613 are applied to an eye 620, or other affected area or region. Alternatively, the irrigation source 616 may be routed to the eye 620 through a separate pathway independent of the handpiece 612. Aspiration is provided from the eye 620 by one or more pumps (not shown), such as a peristaltic pump and/or venturi pump, via the console 606, through lines 622 and 624. A surgeon/operator may select modes of operation of the foregoing, and variables within each mode, via the GUI 604, using the foot pedal 200, and/or by voice command to console 606, by way of non-limiting example.

An interface communications cable 626 connects to the console 606 for distributing instrument data 628, and may include distribution of instrument settings and parameter information, to other systems, subsystems and modules within and external to console 606. Although shown connected to the console 606, interface communications cable 626 may be connected or realized on any other subsystem (not shown) that could accommodate such an interface device able to distribute the respective data.

The embodiments may include at least a footpedal platform 702 upon which footpedal 200 may rest. The footpedal platform 702 may be adjustable and lockable, and may be mounted to a surgeon's chair 704. Mounting to a surgeon's chair may thereby suspend the footpedal slightly off the ground, thus allowing the foot pedal to move freely with the chair.

For example, the doctor may be able to set the footpedal 200, using the adjustment mechanisms 706 provided, to a desired location and height using the platform 702. This adjustment may occur before scrubbing in for surgery, after scrubbing in but before beginning surgery, or during surgery, by way of example. Accordingly, once the footpedal 200 is set, the chair may be moved freely without the need to relocate the footpedal 200 based on movement of the chair 704, as the footpedal 200 will necessarily move with the chair 704 in concert with platform 702.

Wired foot pedals may include conduit along the base of the chair 704 that will allow for convenient movement of the wires associated with the footpedal 200 when the chair 704 is moved. Needless to say, full (such as may include onboard battery power and wireless communications) or partial (such as may have wired power) wireless footpedals 200 may have little or no need for such a conduit. Thus, the embodiments allow for convenient use of both wired and wireless footpedals 200.

Yet further, the platform 702 may provide other aspects that enhance efficiency of use, such as providing a non-slip mating surface 710 for the footpedal 200 such that the footpedal 200 may be held in place without the need for clamps, screws, or the like. Of course, clamps, screws, knobs, and the like may be provided as part of the mating surface 710, such as to allow for both adjustment of the footpedal on the platform and the position of the platform itself without undesired slippage.

Figure 3A:
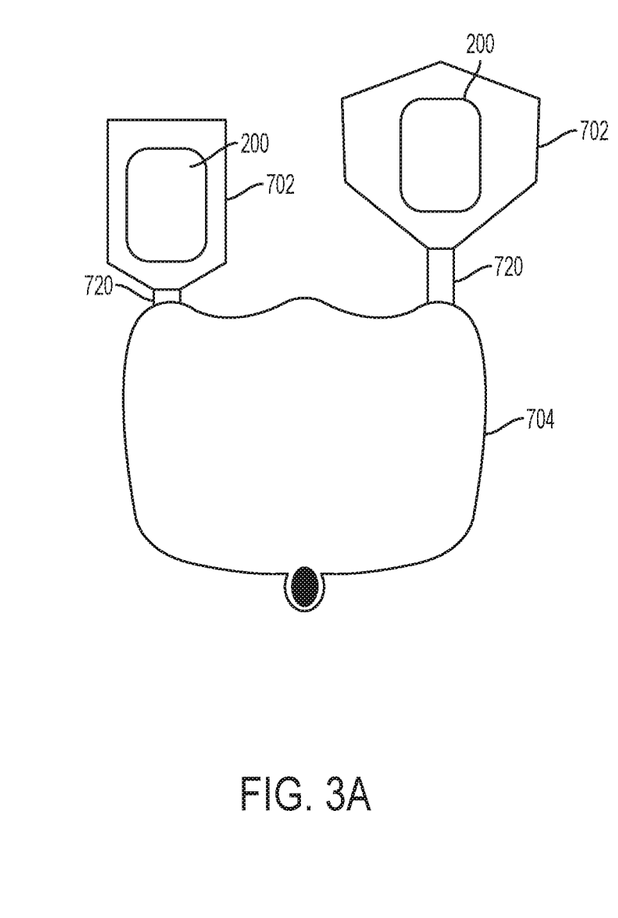
FIGS. 3A and 3B illustrate a surgical chair having fittedly thereon at least one platform for a footpedal.

FIG. 3 illustrate a surgical chair including at least one a platform 702 to enable receipt thereon of a footpedal 200. More particularly, FIG. 3A illustrates cross-sectional top view of a seat of chair 704 having at least one footpedal platform 702 emerging thereunder, supported by bearing arm 720 and having thereon one or more footpedals 200.

Figure 3B:
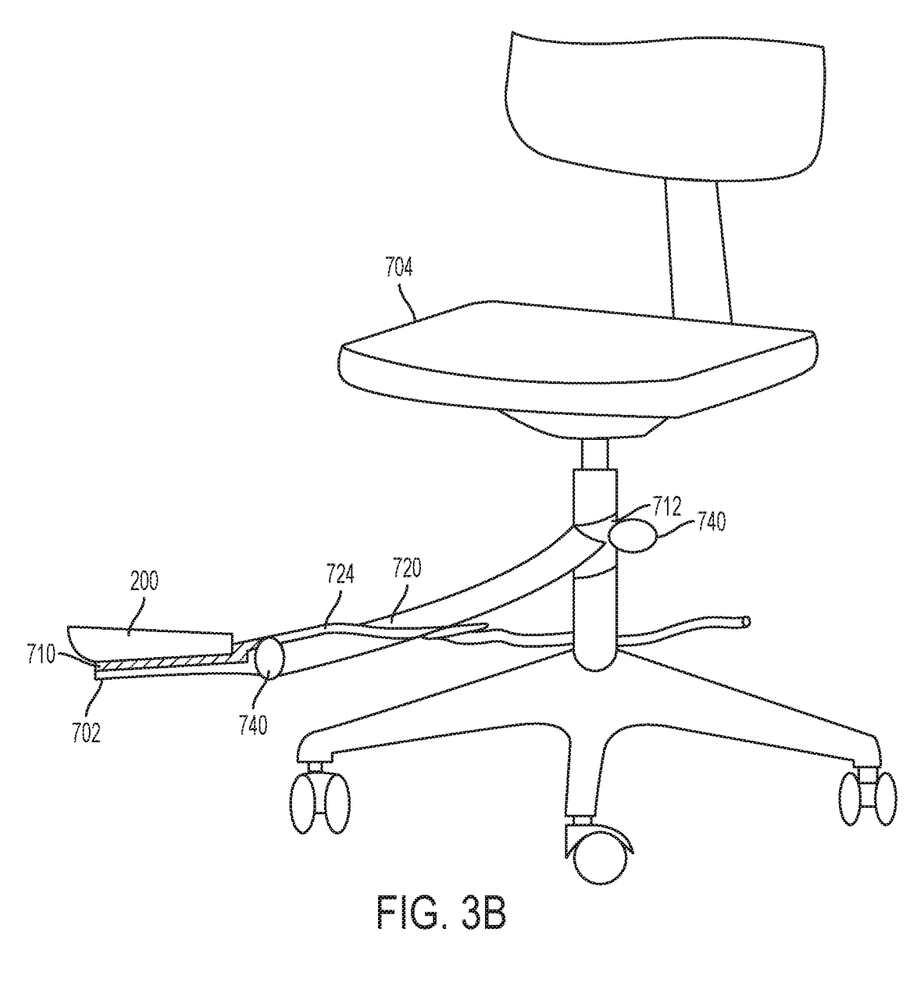

FIG. 3B illustrates a surgical chair 704 having fittedly thereon a platform 702, such as in the form of the illustratively shown "tray", onto which a foot pedal 200 used for surgery may be placed. The platform 702 may, as illustrated, reside on an adjustable bearing arm 720 that may include, at a distal end from the platform 702, a mount 712 to the chair 704. In certain of the embodiments, the platform 702 and/or the bearing arm 720 may be formed of a sturdy, light weight material to allow for ease of inclusion on a chair 704 without undue stress on the chair 704, and to allow for ease of movement of the platform 702 and/or bearing arm 720 as between different chairs, and that will not quickly corrode or otherwise decay when contacted by the environment of and materials in an operating room. Such a material may include, by way of non-limiting example, aluminum.

The mount 712 may removably lock the bearing arm 720 to the chair 704. The mount 712 may be integral with or discrete from bearing arm 720. By way of non-limiting example, the mount 712 may fit at least substantially around the seat post/rigid seat support structure, and may be tightened to the seat post using a screw-in locking mechanism.

Figure 4A:
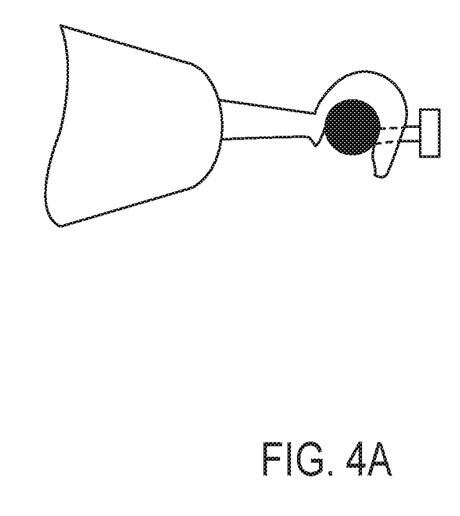
FIGS. 4A and 4B illustrate the mounting of a platform for a surgical pedal to a chair.
Figure 4B:
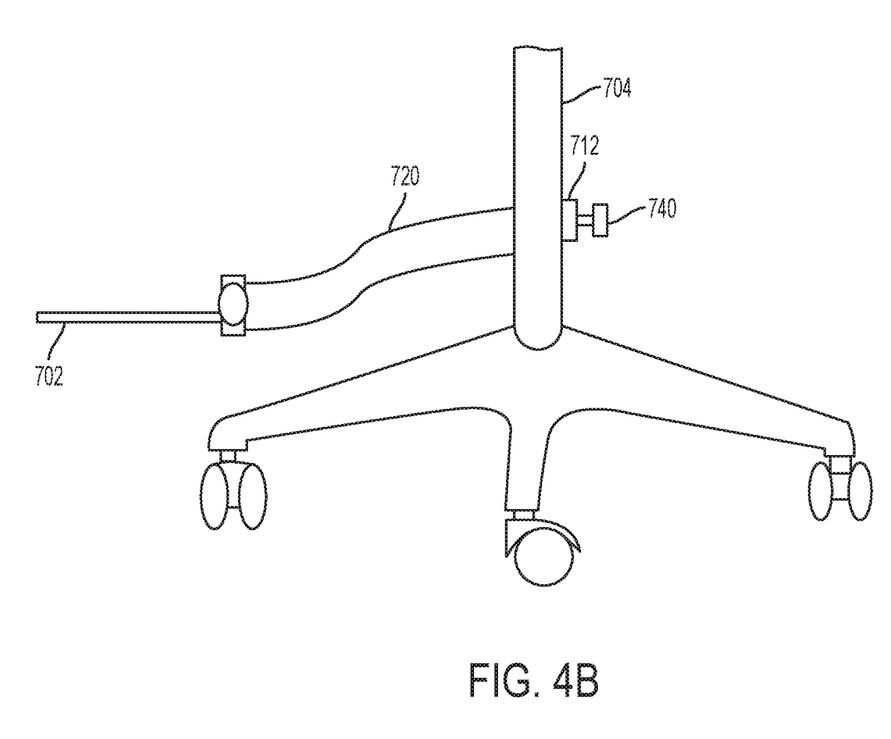

Either or both of the chair mount 712 and/or the platform 702 may provide adjustable features 740 to allow for adjustment, such as in multiple axes with respect to the chair 704. An adjustable feature 740 of mount 712 is illustrated with particularity in the embodiments of FIGS. 4A and 4B. In FIG. 4A, a cross sectional top view of a chair set post/support is shown having a mount 712 with an adjustable feature 740 partially there-around. In FIG. 4B, a side view of the same feature 740 is illustrated. Of note, notwithstanding the exemplary embodiments illustrated in FIG. 4, the bearing arm 720 may mount to the chair 704 on a wheel axle of the chair 704, on the seat support of the chair 704, on the bottom side of the seat of the chair 704, on the backrest of the chair 704, or onto any other aspect of the chair 704.

Moreover, the bearing arm 720 may include conduit 724, such as rotatable conduit 724, to accommodate with wires of a wired footpedal 200. Likewise, the bearing arm 720 may include additional electrical and/or electromechanical elements, such as batteries or remote power for a wireless footpedal, Bluetooth, WiFi, or NFC receivers or repeaters for networked and/or wireless communication, or the like.

Additionally, the platform 702 may include a mounting surface 710, such as a non-slip surface 710, such as a high-friction rubberized surface, for mating with the underside of a footpedal associated therewith, and/or for refined adjustment of the footpedal with respect to the platform 702 and/or the bearing arm 720. That is, sufficient force may overcome the high friction provided by the non-slip surface to allow for movement of the footpedal 200 with respect to the platform, and re-gripping of the footpedal 200 by the platform non-slip surface 710 once the application of the overcoming force ceases.

Thereby, the chair may be set up to the liking of a doctor at the beginning of a surgical day, or at the beginning of each surgery, by way of non-limiting example. Thereafter, such as during a procedure, if the doctor needs to readjust or move the chair, the footpedal will remain in the desired location with respect to the chair, and will move along with the chair when the chair is relocated.

Of course, those skilled in the art will appreciate in light of the discussion herein that the same platform may be enlarged or re-shaped, or an additional platform may be added to the chair, such as to provide optionality for other medical devices used during surgery. For example, the platform may additionally accommodate a surgical microscope-control footpedal that is used during some ophthalmic surgeries. In another embodiment, the platform may be attached to a surgical bed or microscope, thereby allowing the doctor to move the chair freely and come back to the same location.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. An adjustable surgical footpedal system, comprising:
   a bearing arm having a mount;
   a pedal, having associated therewith one or more sensors indicative of at least one surgical setting;
   a platform coupled with a first end of the bearing arm distal from the mount, comprising a mating surface for receiving the pedal; and
   a platform adjustment device configured to adjust the platform in multiple axes,
   wherein the bearing arm further comprises conduit suitable for receiving wiring for connective association with the pedal.

2. The footpedal of claim 1, wherein the platform adjustment device is physically associated with the mount.

3. The footpedal of claim 1, wherein the platform adjustment device is physically associated with the platform.

4. The footpedal of claim 1, wherein the platform adjustment device comprises at least one selected from the group consisting of a knob, a lever, and a screw.

5. The footpedal of claim 1, wherein the mount is suitable for mounting to an axle of a surgical chair.

6. The footpedal of claim 1, wherein the mount is suitable for mounting to one selected from the group consisting of a backrest and a seat of a surgical chair.

7. The footpedal of claim 1, wherein the one or more sensors comprise at least one selected from the group consisting of pneumatic, electrical and mechanical sensors.

8. The footpedal of claim 1, wherein the mating surface is non-slip.

9. The footpedal of claim 1, wherein the platform comprises a tray.

10. A surgical chair, comprising:
    a seat;
    a backrest perpendicularly associated with the seat;
    a plurality of wheels;
    a rigid brace connectively associating the plurality of wheels with the seat;
    a bearing arm having a mount suitable for mounting the bearing arm to the chair;
    a platform at a first end of the bearing arm distal from the mount, comprising a mating surface for receiving a pedal; and
    a platform adjustment device configured to adjust the platform in multiple axes,
    wherein the bearing arm further comprises conduit suitable for receiving wiring for connective association with the pedal.

11. The chair of claim 10, wherein the platform adjustment device is physically associated with the mount.

12. The chair of claim 10, wherein the platform adjustment device is physically associated with the platform.

13. The chair of claim 10, wherein the pedal is associated with one or more sensors indicative of at least one surgical setting and the one or more sensors comprise at least one selected from the group consisting of pneumatic, electrical and mechanical sensors.

14. The chair of claim 10, wherein the mating surface is non-slip.

15. The chair of claim 10, wherein the mounting of the mount is to one selected from the group consisting of an axle associated with the plurality of wheels and the seat.

16. The chair of claim 10, wherein the mounting of the mount is to one selected from the group consisting of the backrest and the rigid brace.

17. The chair of claim 10, wherein the conduit is rotatable.

18. An adjustable platform capable of receiving a surgical footpedal, comprising:
    a bearing arm having at a first end thereof an adjustable mount suitable for mounting to a surgical chair;
    a platform at a second end of the bearing arm distal from the first end, the platform being capable of receiving the surgical footpedal and comprising a mating portion for receiving the surgical footpedal; and
    a platform adjustment device physically associated with the second end of the bearing arm, the platform adjustment device being configured to adjust the platform in multiple axes,
    wherein the bearing arm further comprises conduit suitable for receiving wiring for connective association with the pedal.

19. The adjustable platform of claim 18, wherein the adjustable mount comprises at least one selected from the group consisting of a knob, a lever, and a screw.

20. The adjustable platform of claim 18, wherein the mating portion comprises a non-slip surface.

21. The adjustable platform of claim 18, wherein the platform comprises a tray.

22. The surgical chair of claim 10, wherein the platform adjustment device is a first platform adjustment device physically associated with the mount and the surgical chair further comprises a second platform adjustment device physically associated with the platform.

* * * * *